United States Patent [19]

Lisboa et al.

[11] Patent Number: 5,679,324
[45] Date of Patent: Oct. 21, 1997

[54] AEROSOL FOAMABLE FRAGRANCE COMPOSITION

[75] Inventors: Louis Sergio Lisboa, Cincinnati; Mason Stanley Simmons, West Chester, both of Ohio

[73] Assignee: The Procter & Gamble Co., Cincinnati, Ohio

[21] Appl. No.: 545,194

[22] Filed: Oct. 17, 1995

Related U.S. Application Data

[63] Continuation of Ser. No. 272,169, Jul. 8, 1994, abandoned.

[51] Int. Cl.$^6$ .................................................. A61K 9/12
[52] U.S. Cl. .................... 424/45; 424/73; 424/70.1; 424/78.05; 424/70.16; 514/63; 514/937; 514/938; 514/945; 252/351
[58] Field of Search .................... 424/73, 43, 45, 424/70.1, 78.05, 70.16; 514/63, 937, 938, 945; 252/351

[56] References Cited

U.S. PATENT DOCUMENTS

| | | | |
|---|---|---|---|
| 3,485,915 | 12/1969 | Gerstein et al. | 424/47 |
| 3,719,752 | 3/1973 | Taylor | 424/45 |
| 4,136,163 | 1/1979 | Watson et al. | 424/54 |
| 4,230,688 | 10/1980 | Rowsell et al. | 424/45 |
| 4,304,679 | 12/1981 | Hooper et al. | 424/402 |
| 4,322,308 | 3/1982 | Hooper et al. | 510/101 |
| 4,509,949 | 4/1985 | Huang et al. | 8/558 |
| 4,627,973 | 12/1986 | Moran et al. | 424/47 |
| 4,704,272 | 11/1987 | Oh et al. | 510/122 |
| 4,788,006 | 11/1988 | Bolich | 510/121 |
| 4,919,934 | 4/1990 | Deckner et al. | 424/401 |
| 4,937,370 | 6/1990 | Sabatelli | 560/45 |
| 4,946,671 | 8/1990 | Bissett et al. | 424/59 |
| 5,002,680 | 3/1991 | Schmidt et al. | 510/140 |
| 5,106,609 | 4/1992 | Bolich et al. | 424/70.12 |
| 5,262,154 | 11/1993 | Wendel et al. | 424/73 |

FOREIGN PATENT DOCUMENTS 663003 11/1966 South Africa.

OTHER PUBLICATIONS

Sciarra, John J. and Ward, John B., "New developments in aerosol creams and lotions", *Cosmetics & Toiletries*, vol. 95, 1980, pp. 44–46.

Harrow, Philip A., "Shaving preparations in the patent literature 1970–1975", *Cosmetics and toiletries*, vol. 91, 1976, pp. 18–20.

*Cosmetics & Toiletries*, vol. 100, 1985, pp. 83–89.

*Primary Examiner*—Raj Bawa
*Attorney, Agent, or Firm*—Leonard W. Lewis; William J. Winter

[57] ABSTRACT

The present invention pertains to a low stinging and low burning aerosol foamable fragrance composition, translucent in its pre-dispensed state, which upon discharging from an aerosol container, forms a fast breaking foam. Furthermore, said composition may contain additional ingredients to promote skin moisturization and conditioning. The composition contains surfactant, a propellant, a fragrance, a thickener, and a cosmetic vehicle wherein the ratio of the surfactant to propellant is from about 1:1 to about 1:10.

7 Claims, No Drawings

AEROSOL FOAMABLE FRAGRANCE COMPOSITION

This is a continuation of application Ser. No. 08/272,169, filed on Jul. 8, 1994, now abandoned.

TECHNICAL FIELD

The present invention pertains to a low stinging and low burning aerosol foamable fragrance composition, translucent in its pre-dispensed state, which upon discharging from an aerosol container, forms a fast breaking foam. Furthermore, said composition may contain additional ingredients to promote skin moisturization and conditioning.

BACKGROUND OF THE INVENTION

Cosmetic aerosol foam compositions, particularly those used in association with shaving are well known in the art. Aerosol shaving compositions such as shaving creams and shaving gels have been used for a number of years, with aerosol shaving gels recently gaining wide appeal among both men and women. Published documents including Harrow, *Shaving Preparations In The Patent Literature 1970–1975*, Cosmetics and Toiletries Vol. 91, pp 18–24, July 1976 (incorporated herein by reference) discuss the evolution of aerosol shaving aids including those comprising a transparent, i.e. micellar, dispersion or microemulsion of a hydrocarbon or fluorocarbon propellant in an aqueous solution of a foam-producing surfactant; the propellant being dispersed in the aqueous solution by means of a propellant-soluble water-insoluble surfactant.

In addition to shaving aids, other personal care foam products are well known in the art and include oral hygiene, shower, sun, foot, hand, skin and male fragrance products. Said products are described in Sciarra and Ward, *New Developments In Aerosol Creams and Lotions*, Cosmetics and Toiletries Vol. 95, pp 44–46, March 1980. U.S. Pat No. 4,627,973, Moran et al., issued Dec. 9, 1986 discloses skin and or fragrance compositions in the form of a light and stable foam or mousse which does not readily break down. Said compositions contain a combination of three moisturizers including alkoxylated methyl glucose derivative, an alkoxylated lanolin derivative, and acetylated lanolin alcohol.

South African Patent Application 663003, Lanzet, Published Nov. 16, 1966 teaches making self-propelled homogeneous compositions which are clear in their predispensed form even at low ambient room temperatures. These compositions are thought to be less irritating to the skin based on the fact they contain reduced alcohol levels from about 30% to about 55%. Said compositions additionally comprise water, a solid surfactant blend comprising $C_{12}$ to $C_{22}$ saturated fatty alcohols and a non-ionic surfactant selected from the class consisting of polyethylene oxide derivatives of lanolin acids and lanolin alcohols, and a hydrocarbon propellant.

SUMMARY OF THE INVENTION

The present invention pertains to a low stinging and burning aerosol foamable fragrance composition, translucent in its predispensed state, producing a quick breaking foam upon discharge from an aerosol container. Said aerosol compositions comprise a surfactant, propellant, fragrance, thickner, in a cosmetic vehicle wherein the ratio of the surfactant to propellant is from about 1:1 to about 1:10. This quick breaking aerosol foam disappears rapidly into the skin without stinging and burning said skin. Said compositions may also contain a variety of ingredients to condition and moisturize the skin.

DETAILED DESCRIPTION OF THE INVENTION

The essential as well as the optional components of the present invention are specified below.

Surfactant

The surfactant used in the present invention is selected from the group consisting of ethoxylated lanolin oil derivatives, propoxylated lanolin oil derivatives, and mixtures thereof which correspond to the formula:

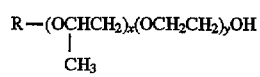

wherein R is selected from the group consisting of the lanolin radical, the hydrogenated lanolin radical and mixtures thereof; x has an average value from about 10 to about 60, preferably from about 30 to about 50, and most preferably about 35 to about 45; and y has an average value from about 20 to about 80, preferably from about 30 to about 70 and most preferably from about 40 to about 65. The level of the above-disclosed surfactants used in the present invention is from about 1.5% to about 4.0%, preferably from about 1.5% to about 2.5%, and most preferably from about 1.75% to about 2.25%.

Said surfactants, also described as emollients derived from lanolin, are generally described in U.S. Pat. No. 4,946,671 Bissett et al., issued August 7, 1990; (incorporated herein by reference). These surfactants are typically water soluble and may be liquid or solid in neat form. A particularly useful surfactants in the present invention is PPG-40-PEG-60-Lanolin Oil available as Aqualose LL100 from Westbrook Lanolin Company, Bradford, England.

Propellant

The propellant used in the present invention are selected from the group consisting of fluorocarbon gases, hydrocarbon gases and mixtures thereof. The level of propellant used in the present invention is from about 2% to about 8%, preferably from about 6.5% to about 7.5%, wherein the ratio of the surfactant to propellant is from about 1:1 to about 1:10, preferably from about 1:1 to about 1:5, and most preferably about 2:7.

Hydrocarbon propellants are preferred in the present invention with the most preferably hydrocarbon propellants conforming to the formula $C_aH_b$ wherein a is from about 1 to about 6, and b is from about 3 to about 14. Said propellants are selected from the group consisting of butane, iso-butane, propane, pentane, and mixtures thereof, and are commercially available from a number of sources. Particularly preferred in the present invention is isobutane/propane available as Propellant A46 from Aeropres Corporation, Shreveport, La.

Fragrance

The compositions of the present invention contain a fragrance or perfume to impart a desired aroma, or to mask odors that may be associated with other components of the compositions. In the present invention the fragrance is used at a level from about 0.1% to about 10%, preferably from about 0.1% to about 7%, more preferably from about 0.1% to about 3%.

Any fragrance suitable for application to the skin can be used herein including a wide variety of fragrances and perfumes that are known to those skilled in the art. The particular perfume used is largely a matter of choice, however, the fragrance should be used at a level effective for providing a noticeable aroma to the composition, or for masking undesired aroma of the composition. Also, the fragrance and whatever carriers accompany it should not impart excessive stinging to the skin, especially broken or irritated skin, at the levels previously disclosed.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308, Hooper et al., issued Mar. 30, 1982, and U.S. Pat. No. 4,304,679, Hooper et al., issued Dec. 8, 1981, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinold and opoponax resinold); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as Coumarin and B-naphthyl methyl ether); esters (such as diethyl phthalate, phenylethyl phenylacetate, non-anolide-1:4). Fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Fragrance used in the present invention may also contain solubilizers, diluents, or solvents which are well known in the art. Such materials are described in Arctander, Perfume and Flavour Chemicals (Aroma Chemicals), Vol. I and II (1969). These materials typically include dipropylene glycol, diethylene glycol, $C_1$–$C_6$ alcohols, and benzyl alcohol.

Thickeners

Thickeners, which also include gellants and suspending agents, are used in the present invention at levels from about 0.015% to about 10.0%, preferably from about 0.05% to about 3.0% and most preferably from about 0.075% to about 0.30%. Said thickhers are selected from the group consisting of carboxylic copolymers, acrylate/alkyl acrylate crosspolymers, alkyl glycols, alkyl modified cellulose polymers, long chain acyl derivative materials, long chain amine oxides, gums, ethylene glycol stearates, alkanol amides of fatty acids, carboxyvinyl polymers, water-soluble or colloidally water-soluble polymers, and mixtures thereof. A preferred thickener for use in the present invention are acrylate/alkyl acrylate crosspolymers.

Acrylate/alkyl acrylate crosspolymers are selected from the group consisting of alkyl acrylate crosspolymer, acrylate copolymers, starch grafted acrylate copolymers, and mixtures thereof. These materials are comprised of one or more monomers of acrylic acid, methacrylic acid or one of their simple esters crosslinked with an allyl ether of sucrose, pentaerythritol, propylene, or mixtures thereof. They may also have starch grafted within the acrylate backbone. Particularly useful in the present invention is acrylates/C10–30 alkyl acrylate crosspolymer. Acrylate/alkyl acrylate crosspolymers include Carbopol Series and the Pemulen Series, both available from B. F. Goodrich, the Acritamer Series, available from RITA, and Sanwet Superabsorbent Polymers, available from Hoechst Celanese. These polymers are more fully described in U.S. Pat. No. 4,509,949, Huang et al., issued Apr. 5, 1985, and U.S. Pat. No. 2,798,053, Brown, issued Jul. 2, 1957, both of which are incorporated herein by reference.

The alkyl modified cellulose polymers suitable as thickners include those selected from the group consisting of methylcellulose, ethylcellulose, hydroxybutyl methylcellulose, hydroxy ethylcellulose, hydroxy propylcellulose, hydroxypropyl methylcellulose cellulose, and mixtures thereof. These and other thickners useful in the present invention are disclosed in U.S. Pat. No. 5,106,609, Bolich et al., issued Apr. 21, 1992, U.S. Pat. No. 5,104,646, Bolich et al., issued Apr. 14, 1992, U.S. Pat. No. 5,100,658, Bolich et al., issued Mar. 31, 1992, and U.S. Pat. No. 5,100,657, Ansher-Jackson et al., issued Mar. 31, 1992, all of which are incorporated herein by reference. These patents disclose thickened vehicle systems containing water, a surfactant or water insoluble polymer, and a nonionic, hydrophobicaliy modified water soluble polymer, such as a nonionic, long chain alkylated (e.g., hydroxyalkyl, urethane, or acyl radicals) cellulosic polymer, e.g., Natrosol Plus CS Grade 67, a hydrophobically modified (cetylated) hydroxyethyl cellulose available from Aqualon Corporation, Wilmington, Del., USA.

Suspending agents include long chain acyl derivative materials, long chain amine oxides, and mixtures thereof. Preferably such suspending agents are present in the composition in crystalline form. Suspending agents of this type are described in U.S. Pat. No. 4,741,855, Grote and Russell, issued May 3, 1988, incorporated herein by reference. Included are ethylene glycol esters of fatty acids preferably having from about 16 to about 22 carbon atoms. More preferred are the ethylene glycol stearates, both mono and distearate, but particularly the distearate. Other suspending agents found useful are alkanol amides of fatty acids, preferably having from about 16 to about 22 carbon atoms, more preferably about 16 to 18 carbon atoms. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives also include N,N-dihydrocarbyl amido benzoic acid and soluble salts thereof (e.g., Na and K salts), particularly N,N-di(hydrogenated) $C_{16}$, $C_{18}$ and tallow amido benzoic acid species of this family, which are commercially available from Stepan Company (Northfield, Ill., USA). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used. The long chain amine oxides are preferably alkyl ($C_{16}$–$C_{22}$) dimethyl amine oxides, e.g., stearyl dimethyl amine oxide. The acyl derivative and amine oxide suspending agents are typically present in pourable, liquid formulations.

Gums are also useful as a thickener in the present invention. Said gums include those commonly known for use in the hair care area, specifically xanthan gum. Shampoo compositions utilizing xanthan gum as a suspending agent for the silicone hair conditioning component are described in U.S. Pat. No. 4,788,006, Bolich and Williams, issued Nov. 29, 1988, incorporated herein by reference. Xanthan gum is biosynthetic gum material that is commercially available. It is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. This information and other is found in Whistler, Roy L. Editor Industrial Gums—Polysaccharides and Their Derivatives New York: Academic Press, 1973. Kelco, a Division of Merck & Co., Inc. offers xanthan gum as KeltrolR.

Combinations of long chain acyl derivatives and xanthan gum are disclosed as a suspending agent for silicone hair conditioners in U.S. Pat. No. 4,704,272, Oh et al., issued Nov. 3, 1987, incorporated herein by reference, and may also be used in the present compositions.

Another thickener useful in the present invention are carboxyvinyl polymers. A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Preferred polyhydric alcohols used to product carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Materials that can also be used as suspension or gelling agents, include water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives.

Cosmetic Vehicle

The present invention employs an cosmetic vehicle or base suitable for topical application to the skin. Said vehicle is used at levels necessary to bring the entire composition to 100%, typically from about 50% to about 98% of the composition. Said vehicle is preferably water, however, additional ingredients may be added to said cosmetic vehicle to obtain various skin feel benefits.

Monohydric alcohols having a carbon chain length from about 1 to 6 may be added to said cosmetic vehicle to obtain a faster evaporation of said vehicle from the skin after application of the foam. Preferred alcohols are selected from the group consisting of methanol, ethanol, propanol, and mixtures thereof. The level of alcohol in said vehicle should be limited to a maximum level so as to avoid excessive stinging and burning upon application to the skin, particularly skin that has been subjected to shaving with a razor. When alcohol is used in the cosmetic vehicle, its level is less than about 10%, preferably less than about 5%, and most preferably less than 1% of the aerosol foamable composition of the present invention.

Optional Ingredients

The composition of the present invention may contain, but are not limited to cosmetically active ingredients medicaments to obtain desirable skin feel benefits. Cosmetically active ingredients are defined herein as compounds or materials which directly affect the appearance, feel, smell, or comfort of the skin, or which protect the skin from environmental factors (e.g., sun light). Medicaments are defined herein as compounds or materials that have a direct medicinal or neurological effect on the body (excluding $C_1$–$C_6$ alcohols). Such materials, well known in the art and are disclosed in the *CTFA Cosmetic Ingredient Handbook*, The Cosmetic, Toiletry, and Fragrance Association, Inc. 1992, pages 658–659.

Cosmetically Active Ingredients

Cosmetically active ingredients include materials for conditioning the skin. Said cosmetically active ingredients include coolants, moisturizers, emollients, sunscreens, pigments and mixtures thereof. Although the exact levels of these ingredients depend on the ingredient or combination of ingredients selected, typically cosmetically active ingredients are used at a levels from about 0.1% to about 20% of the composition.

Skin coolants are particularly useful as a cosmetically active ingredient in the present invention. Said coolants include, but, are not limited to those disclosed in U.S. Pat. No. 4,230,688, Rowsell et al., issued Oct. 28, 1990 (Wilkinson Sword Limited, England) which is incorporated herein by reference; and 3-substituted-p-methanes as described in U.S. Pat. No. 4,136,163 Watson et al., issued Jan. 23, 1979 (Wilkinson Sword Limited, England) which is incorporated herein by reference. Specific coolants used in the present invention are N,2, 3, -trimethyl-2-isopropulbutanamide, N-ethyl p-methan-3-carboxamide, and mixtures thereof at levels from about 0.01% to about 1.0% preferably from about 0.01% to about 0.25% of the composition, wherein the mixture is a ratio of N,2, 3,-trimethyl-2-isopropulbutanamide to N-ethyl p-methan-3-carboxamide from about 1:5 to about 3:1 as disclosed in PCT Application WO 93-05455 published Dec. 23, 1993; incorporated herein by reference.

Skin moisturizers also referred to in the present invention as humectants include urea; guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, hexylene glycol and the like; polyethylene glycol; sugars and starches; sugar and starch derivatives (e.g., alkoxylated glucose); hyaluronic acid; lactamide monoethanolamine; acetamide monoethanolamine; and mixtures thereof.

Emollients useful in the instant invention are further described in U.S. Pat. No. 4,919,934, Deckner et al., issued Apr. 24, 1990, incorporated herein by reference in its entirety. The emollients are preferably used at levels from about 1% to about 10% by weight of the composition. Said emollients include volatile and non-volatile silicone oils, hydrocarbon oils, long chain esters having at least 10 carbon atoms, non-polar carboxylic acid esters, and mixtures thereof. The preferred emollients are nonvolatile, insoluble silicone fluids. These nonvolatile, insoluble silicone fluids will preferably have average viscosity of at least about 1,000, preferably from about 1,000 to about 2,000,000, centistokes at 25° C., more preferably from about 10,000 to about 1,800,000 centistokes, even more preferably from about 100,000 to about 1,500,000 centistokes. Lower viscosity nonvolatile silicone conditioning agents, however, can also be used, as can volatile silicones, and water soluble silicones.

The hydrocarbon oils include esters with hydrocarbyl chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.). Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 19 carbon atoms. Branched chain hydrocarbon oils can and typically may contain higher numbers of carbon atoms. Specific examples include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation.

Long chain fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof.

Non-polar carboxylic acid esters hereof include esters of alcohols and/or acids of the formula R'COOR wherein alkyl or alkenyl radicals and the sum of carbon atoms in R' and R is at least 10, preferably at least 20. The mono non-polar carboxylic acid ester need not necessarily contain at least one chain with at least 10 carbon atoms, so long as the total number of aliphatic chain carbon atoms is at least 10. Examples include diisopropyl adipate, diisohexyl adipate, and diisopropyl sebacate. Di- and tri- carboxylic acid esters can also be used. These include, for example, esters of $C_4$-$C_8$ dicarboxylic acids such as $C_1$-$C_{22}$ esters (preferably $C_1$-$C_6$) of succinic acid, glutaric acid, adipic acid, hexanoic acid, heptanoic acid, and octanoic acid.

Sunscreens and pigments for coloring the skin or aid in tanning of the skin may be used in the present invention and are generally disclosed in U.S. Pat. No. 5,087,445, Haffey et al., issued Feb. 11, 1992; U.S. Pat. No. 5,073,372, to Turner et al., issued Dec. 17, 1991; U.S. Pat. No. 5,073,371, Turner et al., issued Dec. 17, 1991; and Segarin, et al., at Chapter VIII, pages 189 et seq., of Cosmetics Science and Technology, all of which are incorporated herein by reference. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp 38206–38269, Aug. 25, 1978, incorporated herein by reference.

Preferred among those sunscreens disclosed in the above references are those selected from the group consisting of ethylhexyl p-methoxycinnamate, octocrylene, octyl salicylate, oxybenzone, and mixtures thereof. Other useful sunscreens include the solid physical sunblocks such as titanium dioxide (e.g., micronized titanium dioxide, 0.03 microns), zinc oxide, silica, iron oxide and the like. Still other useful sunscreens are those disclosed in U.S. Pat. No. 4,937,370, Sabatelli, issued Jun. 26, 1990 and U.S. Pat. No. 4,999,186, Sabatelli et al., issued Mar. 12, 1991; both incorporated herein by reference.

Medicaments

The medicaments used in the present include, but are not limited to, anti-acne ingredients, antibiotics, antimicrobials, antifungals, antivirals, antibacterials, antiprotozols, anti-inflammatory actives, astringents, antiseptics. Such materials are well known for making compositions at levels to achieve the intended medical effect at the expected unit dosage. The medicaments are preferably used at levels of about 0.1% to about 10% by weight of the composition.

Anti-acne and anti-inflamatory ingredients such as salicylic acid, pantothenic acid and pantothenic acid derivatives (e.g., alcohol, aldehyde, alcohol ester, acid ester derivatives, etc., especially alcohol derivatives such as panthenol). Medicaments particularly useful in the present invention are selected from the group consisting of α racemic bisabolol, d-panthenol, trimethylglycine, and mixtures thereof. Examples of other medicaments include keratolytics such as sulfur, lactic acid, glycolic, pyruvic acid, urea, resorcinol, and N-acetylcysteine; retinoids such as retinoic acid and its derivatives (e.g., cis and trans); antibiotics, antimicrobials, antibacterials, antifungals, antiprotozoals, and antivirals (e.g., benzoyl peroxide, octopirox, erythromycin, tetracyclin, triclosan, azelaic acid and its derivatives, phenoxy ethanol and phenoxy proponol, ethylacetate, clindamycin and meclocycline, triclosan, chlorhexidine, tetracycline, neomycin, miconazole hydrochloride, octopirox, parachlorometaxylenol, nystatin, tolnaftate, clotrimazole, and the like); sebostats such as flavinoids; hydroxy acids; antipruritic drugs including, for example, pharmaceutically-acceptable salts of methdilizine and trimeprazine; and bile salts such as scymnol sulfate and its derivatives, deoxychloate, and cholate.

Also, useful are non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofin, tiaprofenic acid, fluprofen and bucloxic acid. Also useful are the steroidal anti-inflammatory drugs including hydrocortisone and the like.

EXAMPLES

The following examples serve to further describe and demonstrate embodiments within the scope of the invention, but are not to be construed as limitations of the present invention as many variations are possible without departing from the spirit of the invention. The scope of the invention is defined in the claims which follow.

| Ingredient (wt. %) | Examples | | | | | |
|---|---|---|---|---|---|---|
| | 1 | 2 | 3 | 4 | 5 | 6 |
| Fragrance Component | 1.50 | 1.00 | 2.00 | 1.25 | 1.00 | 1.00 |
| Surfactant[1] | 2.00 | 3.00 | 2.50 | 1.50 | 2.00 | 2.00 |
| Alkyl Crosspolymer[2] | 0.15 | 0.25 | 0.50 | 0.15 | 0.30 | 0.15 |
| Butylene Glycol | 1.00 | 1.00 | 1.25 | 1.00 | 0.75 | 1.00 |
| Isobutane | 5.60 | 4.00 | 4.00 | 4.00 | 5.60 | 5.60 |
| Propane | 2.40 | 1.00 | 1.00 | 1.00 | 2.40 | 2.40 |
| Disodium EDTA[3] | 0.10 | 0.10 | 0.10 | 0.10 | 0.10 | 0.10 |
| Ethanol | 5.00 | 3.00 | 0.00 | 0.00 | 0.00 | 0.00 |
| Coolant 1[4] | 0.16 | 0.16 | 0.24 | 0.09 | 0.30 | 0.08 |
| Coolant 2[5] | 0.08 | 0.08 | 0.08 | 0.27 | 0.06 | 0.16 |
| Glydant Plus[6] | 0.20 | 0.20 | 0.18 | 0.22 | 0.20 | 0.20 |
| Sodium Hydroxide | 0.05 | 0.05 | 0.05 | 0.05 | 0.05 | 0.05 |
| Water | | | q.s. to 100% | | | |

[1] PPG-40-PEG-60-Lanolin Oil
[2] Acrylates/C 10–30 Acrylate Crosspolymer
[3] Disodium ethylenediaminetetraacetate
[4] N,2,3-trimethyl-2-isopropybutanamide
[5] N-ethyl p-menthan-3-carboxamide
[6] DMDM hydantoin and iodopropynyl butylcarbamate The above examples are made by mixing Coolants 1 and 2 and the fragrance component to form a solution. A second solution is formed by mixing the water, disodium EDTA, Glydant Plus, and alkyl crosspolymer. The first and second mixtures are then combined wherein the surfactant and butylene glycol are added to the combination. The mixture is then neutralized with sodium hydroxide. This comprises the concentrate. The concentrate is then added to an appropriate aerosol container, sealed, and charged with isobutane/propane to form the finished product.

The compositions can provide a quick breaking foam which has an effective, long-lasting cooling sensation to the skin, low or zero noticeable stinging to the skin, including cut or irritated skin, and a long-lasting smooth, moisturized skin feel.

What is claimed is:

1. An aerosol foamable fragrance composition, translucent in its predispensed state, producing a fast breaking foam upon discharge from an aerosol container comprising:
   a. from about 1.5% to about 4% by weight of a surfactant selected from the group consisting of ethoxylated lanolin oil, propoxylated lanolin oil, and mixtures thereof which correspond to the formula:

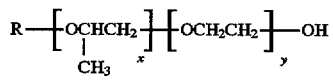

wherein R is selected from the group consisting of the lanolin radical, the hydrogenated lanolin radical and mixtures thereof; x has an average value from about 10 to about 60, and y has an average value of from 20 to about 80;
   b. from about 2% to about 8% by weight of a propellant selected from the group consisting of fluorocarbon gases, hydrocarbon gases and mixtures thereof;
   c. from about 0.1% to about 10% by weight of a fragrance;
   d. from about 0.015% to about 10% by weight of a thickener selected from the group consisting of carboxylic copolymers, acrylate/alkyl acrylate crosspolymers, alkyl glycols, alkyl modified cellulose polymers, long chain acyl derivatives, long chain amine oxides, gums, ethylene glycol stearates, alkanol amides of fatty acids, carboxyvinyl polymers, water-soluble polymers, colloidally water-soluble polymers, and mixtures thereof; and
   e. a cosmetic vehicle containing less than about 10% alcohol by weight of the composition; wherein the ratio of the surfactant to propellant is from about 1:1 to about 1:10.

2. The aerosol foamable fragrance composition according to claim 1 comprising:
   a. from about 1.5% to about 2.5% of a surfactant selected from the group consisting of ethoxylated lanolin oil, propoxylated lanolin oil, and mixtures thereof which correspond to the formula:

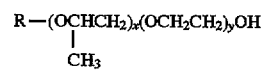

wherein R is selected from the group consisting of the lanolin radical, the hydrogenated lanolin radical and mixtures thereof; x has an average value from about 30 to about 50, and y has an average value from about 30 to about 70;
   b. from about 6.5% to about 7.5% of a hydrocarbon propellant;
   c. from about 1.25% to about 3.0% of a fragrance;
   d. from about 0.15% to about 0.3% of a thickener is an acrylate/alkyl acrylate crosspolymer selected from the group consisting of alkyl acrylate crosspolymer, acrylate copolymers, starch grafted acrylate copolymers, and mixtures thereof; and
   e. an aqueous vehicle containing less than about 5% alcohol; wherein the ratio of said surfactant to propellant is about 1:1 to about 1:5.

3. The aerosol foamable fragrance composition according to claim 2 wherein the vehicle is alcohol free.

4. An aerosol foamable fragrance composition according to claim 3 wherein the propellant is a hydrocarbon conforming to the formula $C_aH_b$ wherein a is from about 1 to about 6, b is from about 3 to about 14.

5. The aerosol foamable fragrance composition according to claim 4 wherein the surfactant is at a level from about 1.75% to about 2.25% wherein x has an average value from about 35 to about 45; and y has an average value from about 40 to about 65.

6. An aerosol foamable fragrance composition, translucent in its predispensed state, producing a fast breaking foam upon discharge from an aerosol container comprising:
   a. from about 1.75% to about 2.25% PPG-40-PEG-60 Lanolin Oil
   b. from about 6.5% to about 7.5% isobutane/propane propellant;
   c. from about 0.1% to about 3% fragrance;
   d. from about 0.075% to about 0.30% acrylates/C10–30 alkyl acrylate crosspolymer; and
   e. an alcohol-free aqueous vehicle wherein the ratio of the surfactant to propellant is from about 2:7.

7. The aerosol foamable fragrance composition according to claim 6 additionally comprising:

a. from about 0.01% to about 0.25% coolant selected from the group consisting of N,2, 3,-trimethyl-2-isopropubutanamide, N-ethyl p-methan-3-carboxamide, and mixtures thereof wherein the mixture is a ratio of N,2, 3,-trimethyl-2-isopropulbutanamide to N-ethyl p-methan-3-carboxamide from about 1:5 to about 3:1;

b. from about 0.01% to about 10.00% of an anti-inflammatory selected from the group consisting of α racemic bisabolol, d-panthenol, trimethylglycine, and mixtures thereof; and c. from about 0.1% to about 10% of a nonvolatile insoluble silicone fluid having an average viscosity from about 1,000 to about 2,000,000, centistokes at 25° C.

* * * * *

UNITED STATES PATENT AND TRADEMARK OFFICE
CERTIFICATE OF CORRECTION

PATENT NO. : 5,679,324

DATED : October 21, 1997

INVENTOR(S) : Louis Sergio Lisboa and Mason Stanley Simmons

It is certified that error appears in the above-identified patent and that said Letters Patent is hereby corrected as shown below:

At column 2, line 10 "Suffactant" should read --Surfactant--.

At column 3, line 22 "resinold" should read --resinoid--.

At column 3, line 23 "resinold" should read --resinoid--.

At column 3, line 59 "thickhers" should read --thickeners--.

At column 4, lines 32-33 "hydrophobicaliy" should read --hydrophobically--.

At column 10, line 7 "derivatives" should read --derivative materials--.

Signed and Sealed this

Sixth Day of October, 1998

*Attest:*

BRUCE LEHMAN

*Attesting Officer*     Commissioner of Patents and Trademarks